United States Patent
Poo et al.

(10) Patent No.: US 7,713,686 B2
(45) Date of Patent: May 11, 2010

(54) ORGAN PRESERVATION CONTAINER AND METHOD

(75) Inventors: Ramon E. Poo, Miami, FL (US); Camillo Ricordi, Miami, FL (US)

(73) Assignees: Biorep Technologies, Inc., Miami, FL (US); University of Miami, Miami, FL (US)

( * ) Notice: Subject to any disclaimer, the term of this patent is extended or adjusted under 35 U.S.C. 154(b) by 1185 days.

(21) Appl. No.: 11/003,808

(22) Filed: Dec. 3, 2004

(65) Prior Publication Data
US 2006/0121437 A1    Jun. 8, 2006

(51) Int. Cl.
*A01N 1/00*    (2006.01)
*A01N 1/02*    (2006.01)

(52) U.S. Cl. .................. 435/1.2; 435/1.1; 435/268; 435/284.1; 210/515

(58) Field of Classification Search .................. 435/1.2, 435/268, 284.1; 210/515; 422/265
See application file for complete search history.

(56) References Cited

U.S. PATENT DOCUMENTS

| | | | |
|---|---|---|---|
| 4,224,707 A * | 9/1980 | Mariani | 441/11 |
| 4,714,595 A | 12/1987 | Anthony et al. | |
| 4,723,974 A * | 2/1988 | Ammerman | 62/4 |
| 4,879,283 A * | 11/1989 | Belzer et al. | 435/1.2 |
| 5,066,578 A | 11/1991 | Wikman-Coffelt | |
| 5,328,821 A * | 7/1994 | Fisher et al. | 435/1.3 |
| 5,498,427 A | 3/1996 | Menasche | |
| 6,490,880 B1 | 12/2002 | Walsh | |
| 6,492,103 B1 | 12/2002 | Taylor | |
| 6,673,594 B1 | 1/2004 | Owen et al. | |
| 6,899,850 B2 * | 5/2005 | Haywood et al. | 422/102 |
| 7,147,826 B2 * | 12/2006 | Haywood et al. | 422/102 |

FOREIGN PATENT DOCUMENTS

EP    1 129 656 A1    9/2001

OTHER PUBLICATIONS

K.-Y. chung, S.H. Sung, Y.S. Kim, K.B. Choi and Y.M. Choi. "Short-term Preservation of Liver with Euro-Collins or UW Solution in Canine Partial Liver Autotransplantation" Transplatation Proceedings, vol. 35, issue 1, pp. 120-121, Feb. 2003. (available online Feb. 12, 2003).*

* cited by examiner

*Primary Examiner*—Michael A Marcheschi
*Assistant Examiner*—Michael Hobbs
(74) *Attorney, Agent, or Firm*—Novak Druce + Quigg LLP; Gregory A. Nelson

(57) ABSTRACT

An organ preservation container includes a gas impermeable housing for containing an organ. At least two liquids having different densities and forming a liquid-liquid interface are also contained in the housing. A closure for hermetically sealing the housing is provided. A structure is provided within the housing for engaging the organ and for maintaining a portion of the organ at the liquid-liquid interface such that the organ will be maintained partially in both of the liquids. A method for preserving the organ is also described.

25 Claims, 12 Drawing Sheets

ORGAN PRESERVATION CONTAINER AND METHOD

BACKGROUND OF THE INVENTION

The period between harvesting an organ and transplantation of the organ or cells from the organ into the recipient usually involves cold storage and transportation. During this period, the supply of blood, and consequently oxygen, is cut off from the organ. This period of cold ischemia is, at present, unavoidable and results in the gradual deterioration of cell function, eventually progressing to irreversible damage.

A new rapidly emerging technique for improved preservation of donor pancreata and possibly other organs has been established and several groups are now testing it in research and clinical trials. The technique is called the 2 layer method and calls for the utilization of a solution of perfluorocarbon (PFC) or other oxygen-dissolving solution in combination with a cold storage preservation solution such as the University of Wisconsin preservation solution (the "UW solution"). The UW solution contains as its primary agents lactobionate and raffinose. These compounds are too large to enter the cells and therefore remain in the extracellular spaces. These impermeants act through osmotic forces to prevent cell swelling that would otherwise damage the stored organ.

Liver is another common organ for transplantation, as transplantation can be the only option for many patients suffering from treatable liver diseases. A successful transplantation requires that the donor liver be optimally preserved. Although the liver can be preserved for 10-20 h, its cellular energy levels fall to critically low values within the first 1-4 h. The consequences of a poorly functioning transplanted liver are potentially fatal, and requires retransplantation at a significant increase in cost. It is therefore vital that adequate procedures and systems be provided for organ storage and transportation.

It is a well known fact that maintaining an organ partially submerged in oxygenated PFC greatly extends its useful life for transplantation or for cell procurement. The density of most organs is approximately 1 g/cm$^3$. The density of PFC is approximately 2 times that of the organ or 1.95 g/cm$^3$ and the density of the UW solution is approximately equal to that of the organ. Accordingly, the PFC settles at the bottom of the container while the UW solution settles on top of it. The organ typically rests partially submerged in the PFC while also being contacted by the UW solution. It is difficult to maintain this partial submersion especially during transportation of the organ because of the different sizes and shapes of organs and because the position of the container may also change.

Walsh, U.S. Pat. No. 6,490,8890, discloses a regulated organ containment shipping system using dual-layer preservation liquid. The organ containment shipping system has an outer container adapted to receive a passive cooling medium and an inner container positioned within the outer container by structure that includes a gimbal mechanism to substantially maintain the inner container in a predefined orientation in the event of a change of orientation of the outer container.

SUMMARY OF THE INVENTION

An organ preservation container comprises a gas impermeable housing for containing the organ in two liquids having a liquid-liquid interface, preferably a preservation solution, and an oxygen-dissolving solution. A closure is provided for hermetically sealing the housing. Structure within the housing is provided for maintaining the organ partially in the oxygen-dissolving solution and partially in the preservation solution. The structure is not connected to the housing and is rotatable with respect thereto.

The structure for maintaining the organ partially in the oxygen-dissolving solution and partially in the preservation solution can comprise ballast structure. The ballast structure can be a permeable enclosure for the organ. The enclosure has a density less than one of the solutions and greater than the other, such that the enclosure will assist in maintaining the organ partially in one of the solutions and partially in the other solution.

The density of the enclosure can be adjusted by providing an enclosure of a first material and weights having a density greater than the first material. The enclosure preferably has an average density between about 1.5-2.5 g/cm$^3$ and preferably has an average density of about 2 g/cm$^3$. The enclosure can have different sizes and shapes. In one aspect, the enclosure has a top portion and depending side portions. At least the top portion is preferably liquid permeable to allow the solutions to freely contact the organ. In one embodiment, the density of the structure preferably is selected to maintain about ⅔ of the mass of the organ in an oxygen-dissolving solution and about ⅓ of the mass of the organ in a preservation solution.

The organ preservation container can have structure for engaging the organ. This structure can be an enclosure that is not connected to the housing. The enclosure is rotatable with respect to the housing, such that the enclosure can right itself when the housing is tilted from the upright position in almost any direction.

The container can have a substantially spherical interior volume. The substantially spherical interior volume permits the enclosure to freely rotate when the container is tilted in one direction or another, to facilitate maintaining contact of the organ with the oxygen-dissolving solution and the preservation solution.

The structure for engaging the organ can comprise a holder for the organ. The holder applies a force to the organ that is selected to maintain the organ partially in both of the liquids. A spring can be used to apply the force to the holder and the organ. The spring has a force selected to maintain the organ partially in both of the liquids.

The structure for engaging the organ can comprise an enclosure having a top portion and a bottom portion. The top portion and the bottom portion can comprise apertures for permitting the ingress and egress of liquid. The bottom portion can comprise ballast, such that the organ is held within the enclosure and is maintained partially in both of the liquids.

The oxygen-dissolving solution can be any suitable solution. Perfluorocarbon is a suitable oxygen-dissolving solution. The preservation solution can also be any suitable preservation solution. The University of Wisconsin solution is a suitable preservation solution.

A method for preserving organs comprises the steps of providing an organ preservation container with a gas impermeable housing for containing the organ, and at least two liquids forming a liquid-liquid interface. A closure is provided for hermetically sealing the housing. Structure within the housing is provided for maintaining the organ partially in both of the liquids. The structure is not connected to the housing and is rotatable with respect thereto. The organ is placed in the housing in contact with the structure for maintaining the organ partially in both of the liquids. The housing is then hermetically sealed with the closure.

The organ is preferably placed within an enclosure which is positioned within the housing. The enclosure has a density that is selected to maintain the organ at a desired location relative to the liquid-liquid interface, partially in each liquid. The enclosure is adapted to permit contact of the organ with the liquids. The liquids preferably comprise an oxygen-dissolving solution and a preservation solution. The average density of the enclosure is preferably selected to maintain about ⅔ of the organ in the oxygen-dissolving solution and about ⅓ of the organ in the preservation solution.

BRIEF DESCRIPTION OF THE DRAWINGS

There are shown in the drawings embodiments which are presently preferred, it being understood, however, that the invention is not limited to the precise arrangements and instrumentalities shown, wherein.

DETAILED DESCRIPTION OF THE INVENTION

Figure 1:
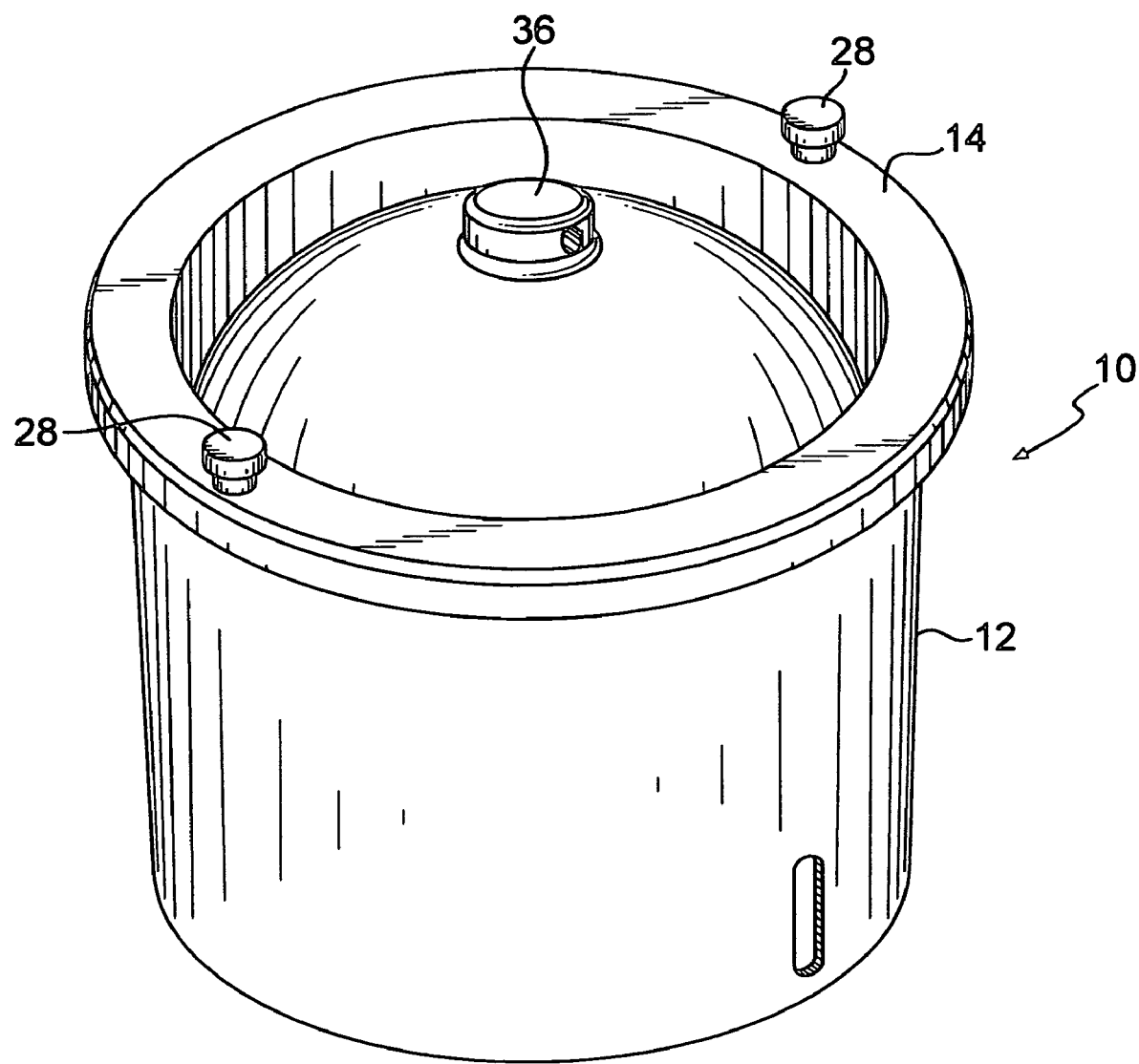
FIG. 1 is a perspective view of an organ preservation container according to the invention.
Figure 2:
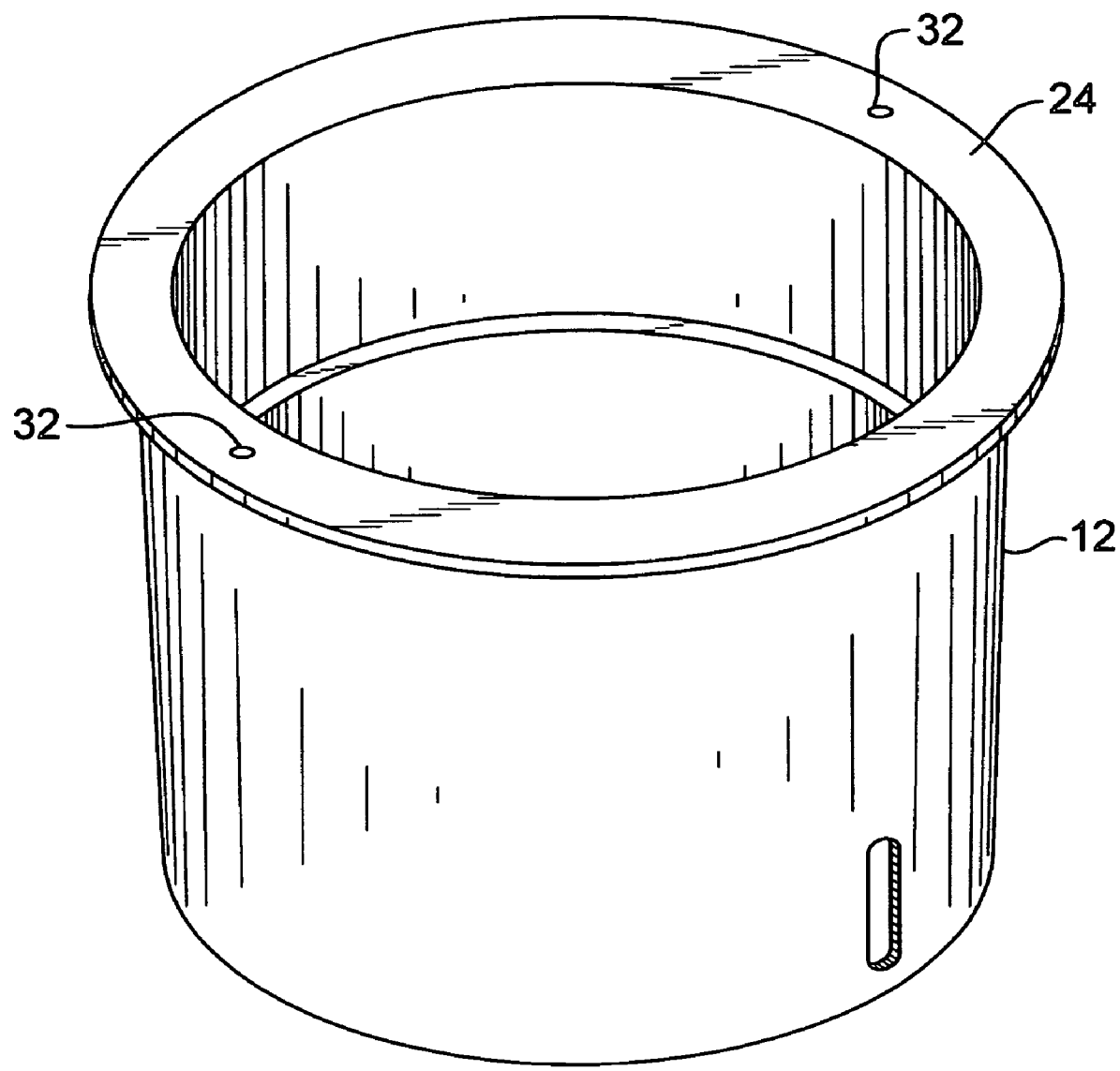
FIG. 2 is a perspective view of a housing.
Figure 3:
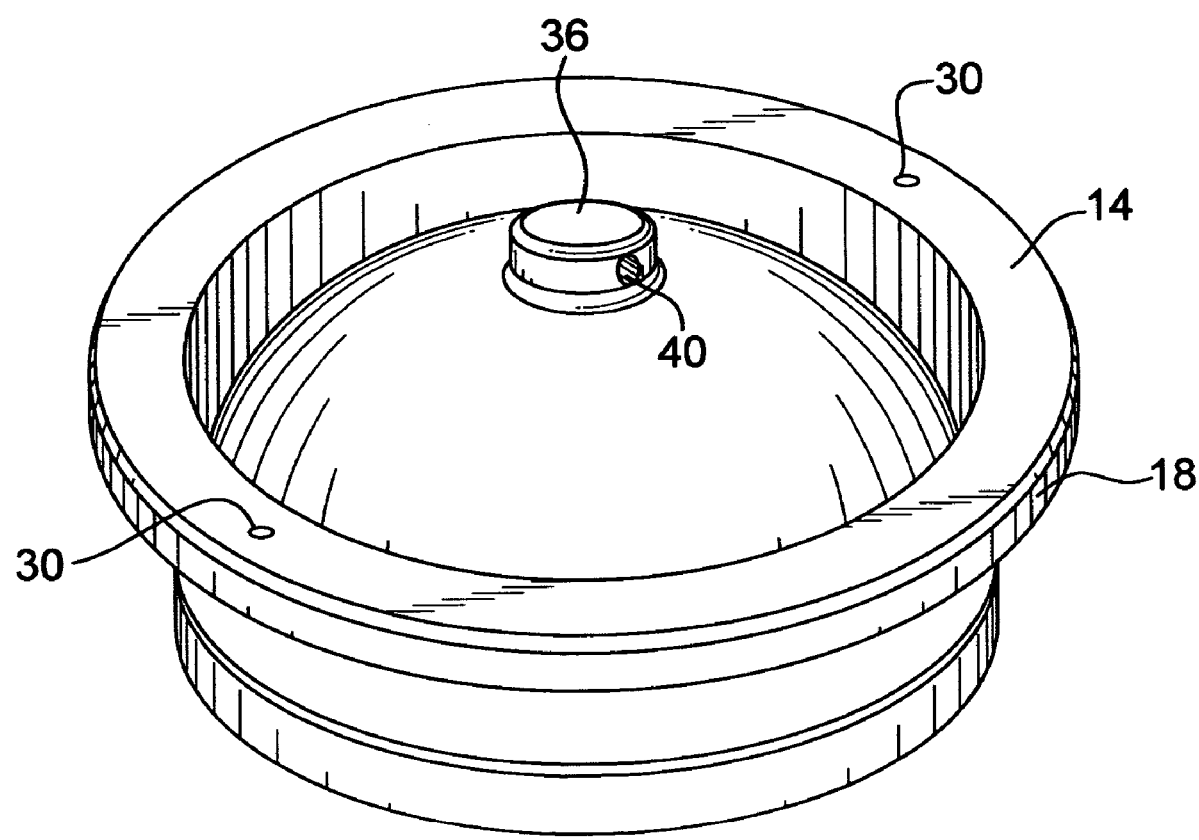
FIG. 3 is a perspective view of a closure for the housing.
Figure 4:
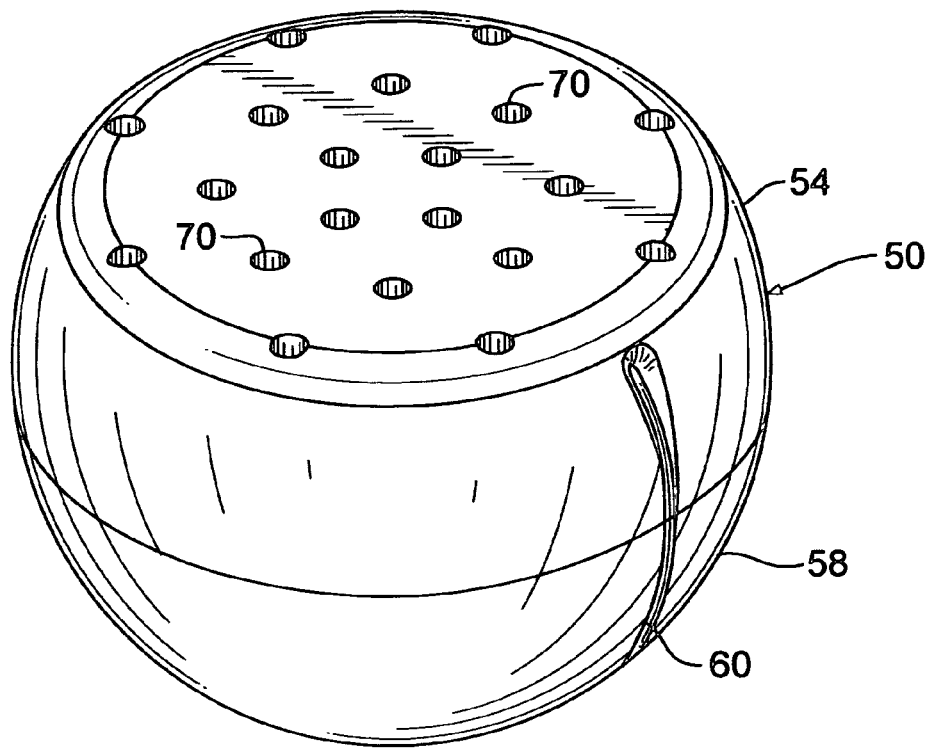
FIG. 4 is a perspective view of an enclosure for an organ.
Figure 5:
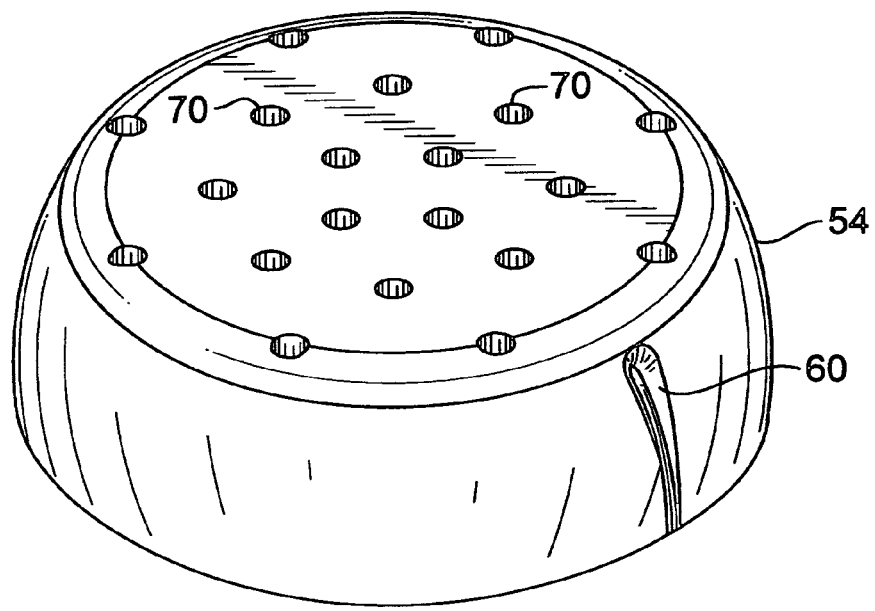
FIG. 5 is a perspective view of a top portion of the enclosure.
Figure 6:
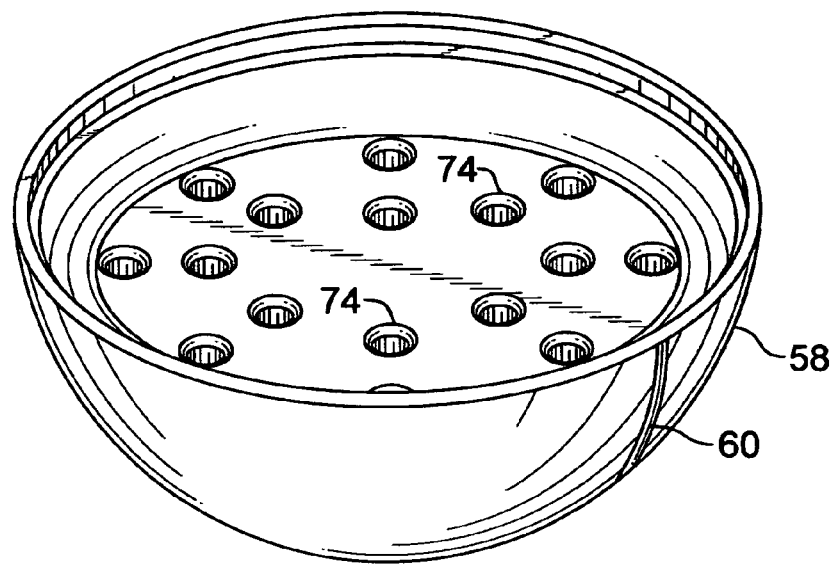
FIG. 6 is a perspective view of a bottom portion of the enclosure.
Figure 7:
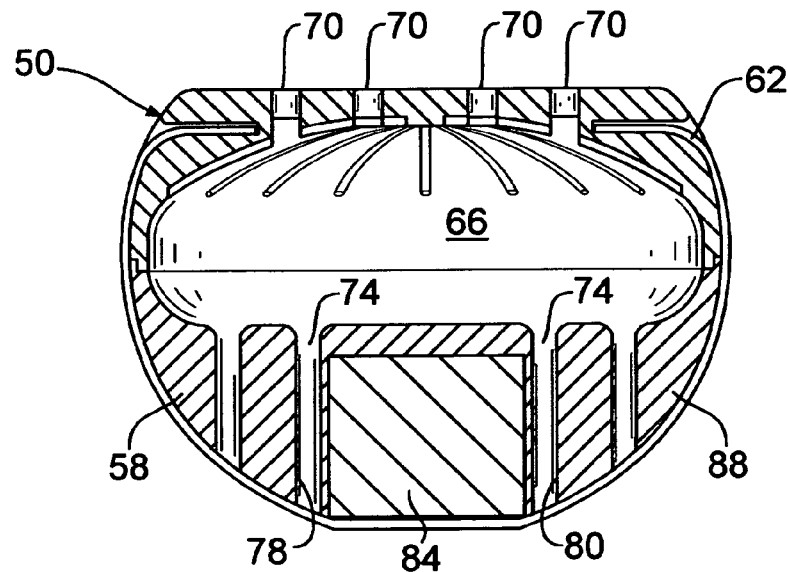
FIG. 7 is a cross-sectional view of the enclosure.
Figure 8:
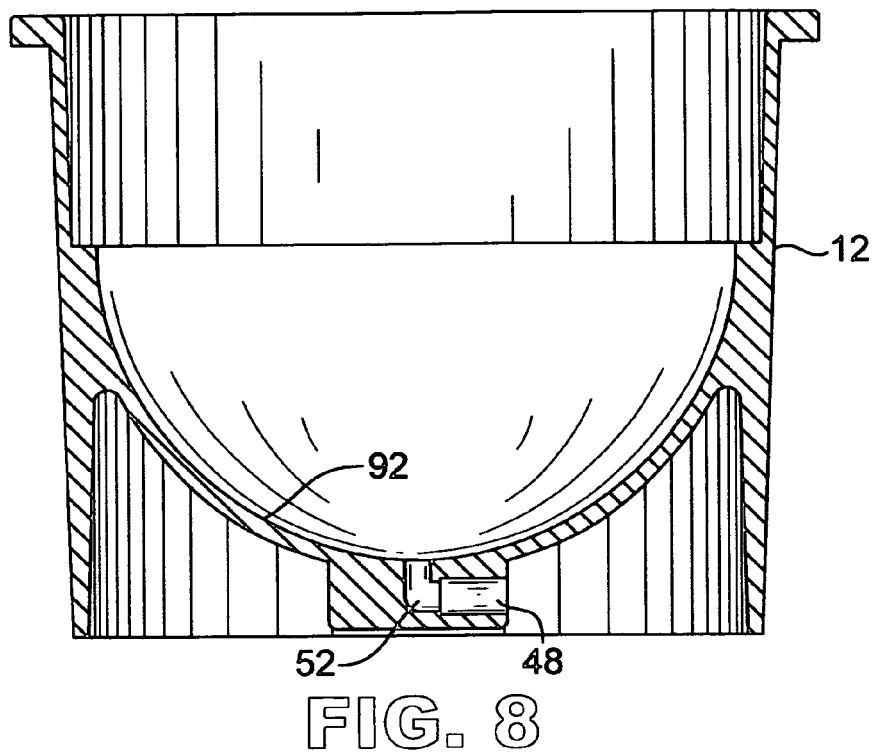
FIG. 8 is a cross-sectional view of the housing.

There is shown in FIGS. 1-11, a container 10 for preserving organs. The container 10 has a housing 12 and a closure 14 for hermetically sealing the housing 12. The housing 12 contains a dual layer liquid composition which forms a liquid-liquid interface. The liquid can be a preservation solution and an oxygen-dissolving solution, although other solutions are possible. The closure 14 can be engaged to the housing 12 by any suitable structure. In one aspect, the closure 14 has a flange 18 which mates against a flange 24 of the housing 12. Suitable structure, such as threaded fasteners 28, can be provided and can engage suitable cooperating apertures 30 in the closure 14 and apertures 32 in the housing 12 to secure the closure 14 to the housing 12. Alternative sealing structure, such as O-rings and gaskets can be provided. Alternative means of securing the closure 14 to the housing 12 are possible, for example, the closure 14 and housing 12 can comprise cooperating threaded engagement structure and the closure 14 can be screw-fit to the housing 12.

Structure can be provided for supplying fluid into the housing after the closure 14 is in place. A first port 36 in the closure 14 can have a fitting 40 connecting to conduit 42 for supplying fluid into the organ preservation container 10. A second fluid port 44 can be provided in the housing 12. The second port 44 can have a fitting 48 connecting to an conduit 52 for supplying a second fluid to the organ preservation container 10.

The organ is held within the container by an enclosure which maintains the organ in the enclosure in a position such that the organ is maintained partially in the first liquid and partially in the second liquid. The enclosure is not connected to the housing 12 and can thereby rotate with respect thereto. Different enclosure constructions are possible. There is shown in FIGS. 4-7 an enclosure 50 according to one embodiment of the invention. The enclosure 50 has a top portion 54 and a bottom portion 58. The top portion 54 can be joined to the bottom portion 58 by any suitable structure. In one embodiment, groove 60 is provided to receive C-clip 62 to secure the top portion 54 to the bottom portion 58. Other joining structure is possible.

The enclosure 50 has an open interior 66 to receive the organ. The open interior 66 can be formed by mating open portions of the top portion 54 and bottom portion 58. Other constructions are possible. Apertures are provided to permit the ingress and egress of fluid into the enclosure 50. Apertures 70 can be provided in the top portion 54. Similarly, apertures 74 can be provided in the bottom portion 58. The apertures 74 can be provided as part of elongated channels 78 through the bottom portion 58 which communicate with exterior openings 80. In this manner, fluid can flow into and out of the openings 80 and through the channel 78 and apertures 74 to contact an organ in the interior space 66. Other structure is possible. Ballast 84 can be provided in the bottom portion 58 for adjusting the average density of the enclosure 50 such that an organ within the open interior 66 will be properly positioned at the interface of the two liquids. The ballast 84 can be selected from metal, ceramic, plastic, or other suitable materials.

The average density of the enclosure 50 will be selected for the particular solutions, organ, and organ size that are being utilized. The enclosure 50 should maintain the organ partially in one liquid and partially in the other. Accordingly, the enclosure 50 must position the organ at the interface of the two liquids. In the case where one solution is a preservation solution and the other solution is an oxygen-dissolving solution, it has been found to be preferable that the organ be positioned such that about ⅔ of the organ volume is in the oxygen-dissolving solution and the remaining ⅓ of the organ volume is in the preservation solution. A common oxygen-dissolving solution, perfluorocarbon (PFC), has a density of about 1.95 g/cm$^3$. A common preservation solution, University of Wisconsin Solution, has a density of about 1 g/cm$^3$. The density of most organs is about 1 g/cm$^3$. The organ will tend to rest on top of the more dense oxygen-dissolving solution, and will not properly contact this solution. The average density of the enclosure 50 is selected so as to rest in the more dense solution and maintain the organ at the proper position in the interface. In one embodiment, the enclosure has a density of between 1.5-2.5 g/cm$^3$. In the case where the liquids have densities of 1 g/cm$^3$ and 1.95 g/cm$^3$, respectively, the enclosure preferably has a density of about 2 g/cm$^3$. It will be apparent, however, that differently sized organs and different solutions, as well as different enclosure materials having different densities, will require adjustment in order to properly position the organ. Such adjustments can be made in one aspect by the provision of incremental ballast elements, which can be added or taken away as needed.

Figure 9:
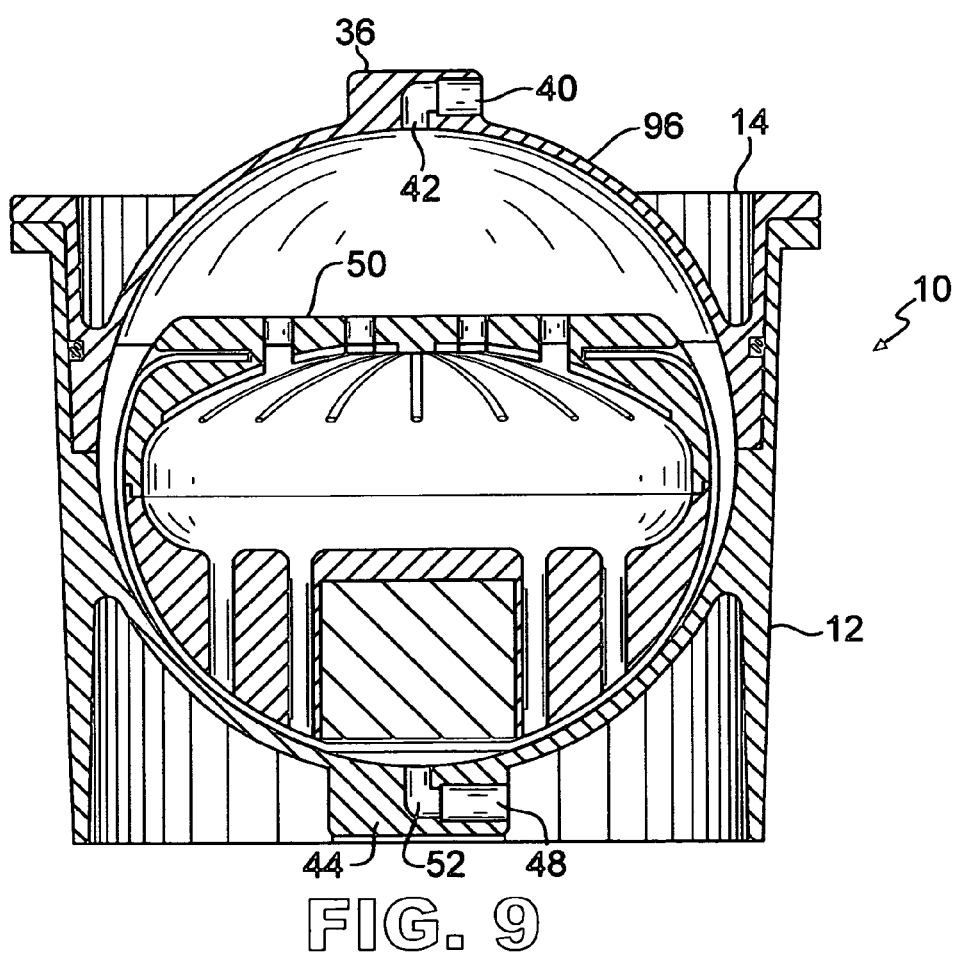
FIG. 9 is a cross-sectional view of the enclosure within the housing, and with the closure covering the housing.

The enclosure 50 is not connected to the housing 12 and, accordingly, can rotate with respect thereto. In order to facilitate such rotation, it is possible to provide that the exterior surface 88 of the enclosure 50 be at least partially spheroidal. An inside surface 92 of the housing 12 can be concave (FIG. 8), such that the enclosure 50 can be positioned in the housing 12 and can rotate within the housing 12 in the event that the housing 12 is tilted from the vertical. The closure 14 similarly can have a concave interior surface 96 to allow such rotation of the enclosure 50 within the housing 12 (FIG. 9). Upon tilting of the housing 12, the liquid interface will remain substantially horizontal and the suspended enclosure 50 will thereby be permitted to rotate within the housing 12 such that the organ will be maintained substantially horizontal at the liquid interface irrespective of the position of the housing 12. The organ 100 will thereby be properly positioned in the open interior 66 of the enclosure 50.

Figure 10:
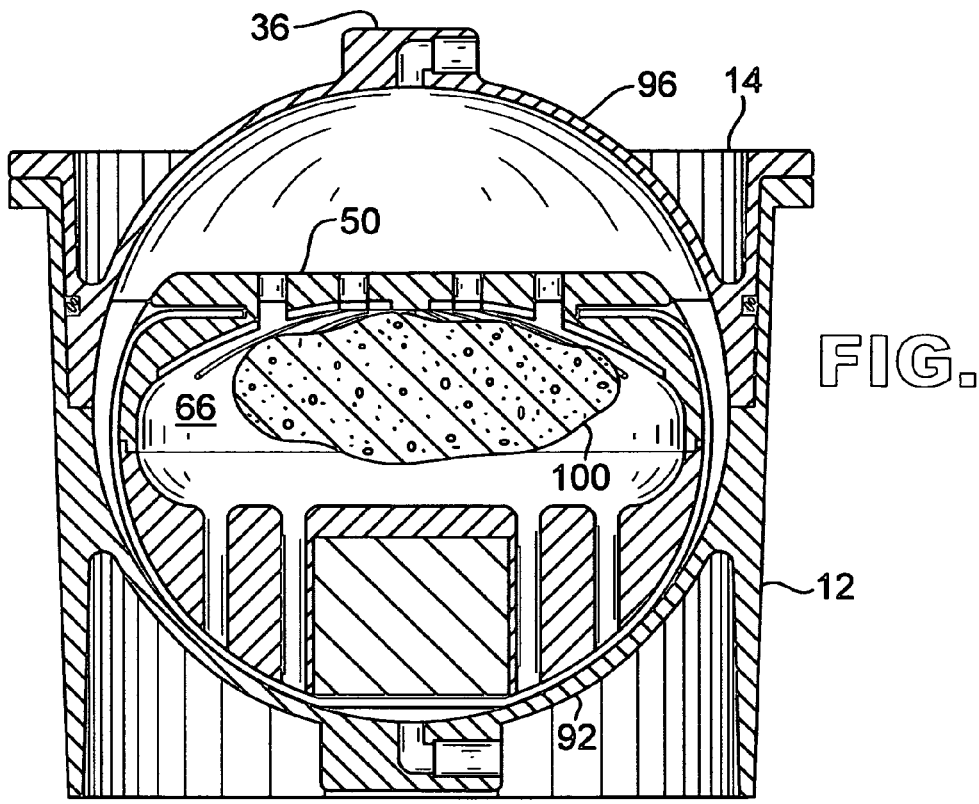
FIG. 10 is a cross-sectional view of the enclosure within the housing, and an organ in the closure, in a first position.
Figure 11:
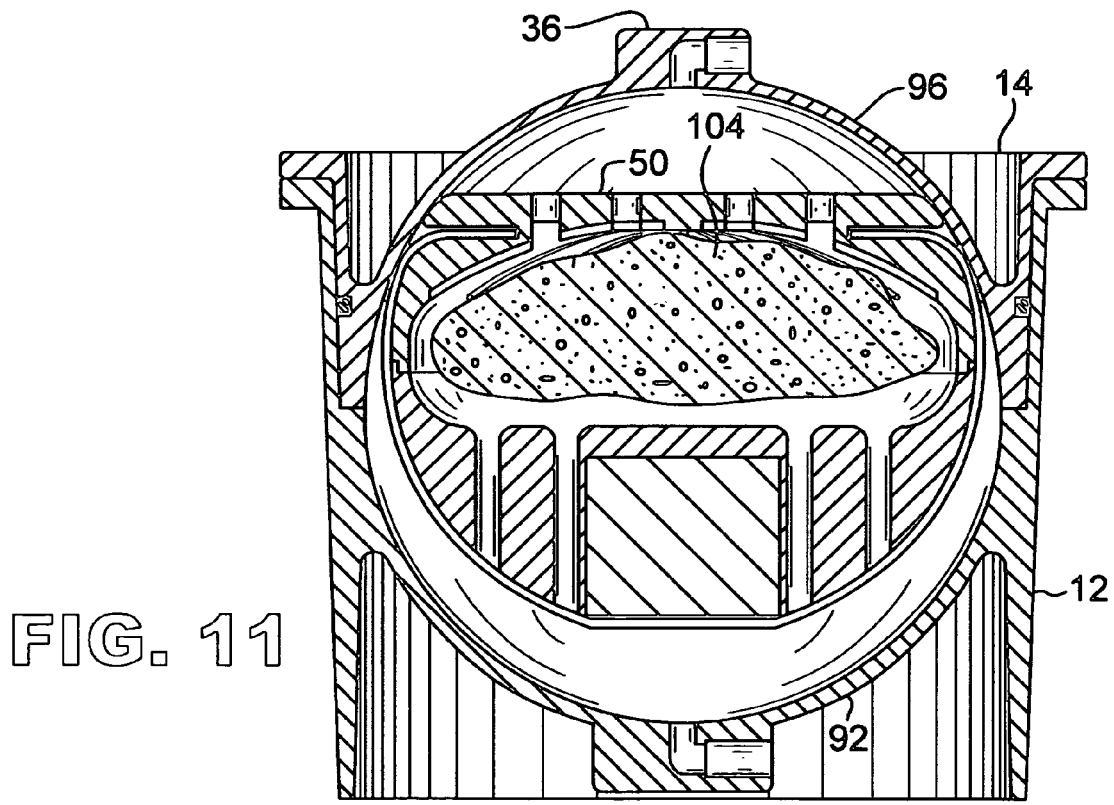
FIG. 11 is a cross-sectional view of the enclosure in the housing and a large organ in the enclosure, the enclosure being in a second position.
Figure 12:
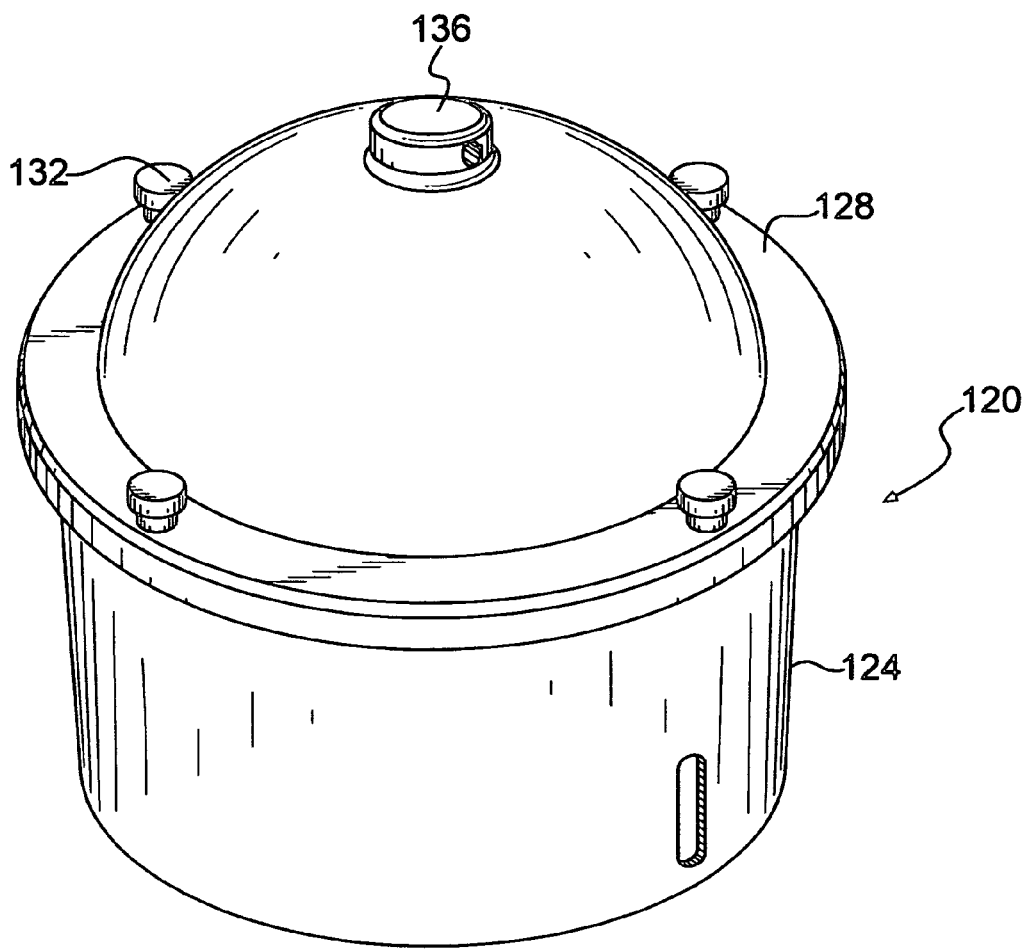
FIG. 12 is a perspective view of an organ preservation container according to an alternative embodiment.

As the organ 100 is less dense than the perfluorocarbon, a larger organ 104 will tend to position itself differently than a smaller organ 100. There is shown in FIG. 10 an organ 100 and in FIG. 11 a larger organ 104. The enclosure 50 in FIG. 10 is positioned further toward the bottom 92 of the housing 12. The larger organ 104 shown in FIG. 11 will float higher relative to the heavier perfluorocarbon solution and the construction of the invention will permit the enclosure 50 to properly position the large organ 104 at the interface between the two liquids.

There is shown in FIGS. 12-16 an alternative embodiment in which an organ preservation container 120 has a housing 124 and a closure 128. Suitable fastening members such as bolts 132 can be provided to secure the closure 128 to the housing 124. Fluid inlet ports 136 and 138 can be provided as previously described. These ports can be used to add liquids or gases, such as oxygen, to oxygenate the oxygen-dissolving solution. The fluids are preferably added through the bottom port 138 until fluid emerges from the top port 136. The system is then closed by suitable structure such as valves.

Figure 13:
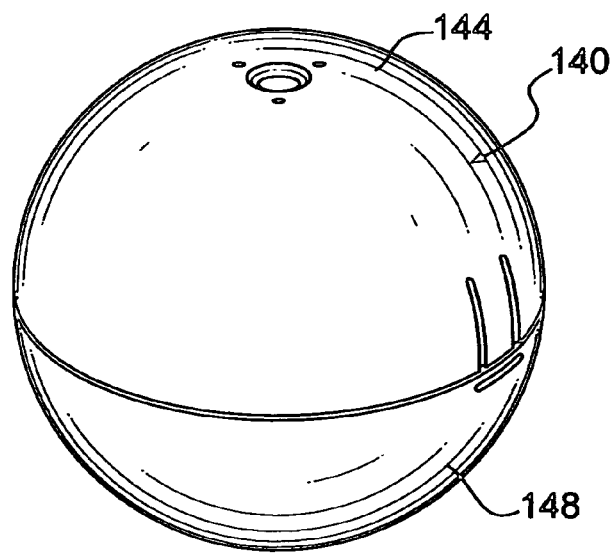
FIG. 13 is a perspective view of an enclosure according to the alternative embodiment.
Figure 14:
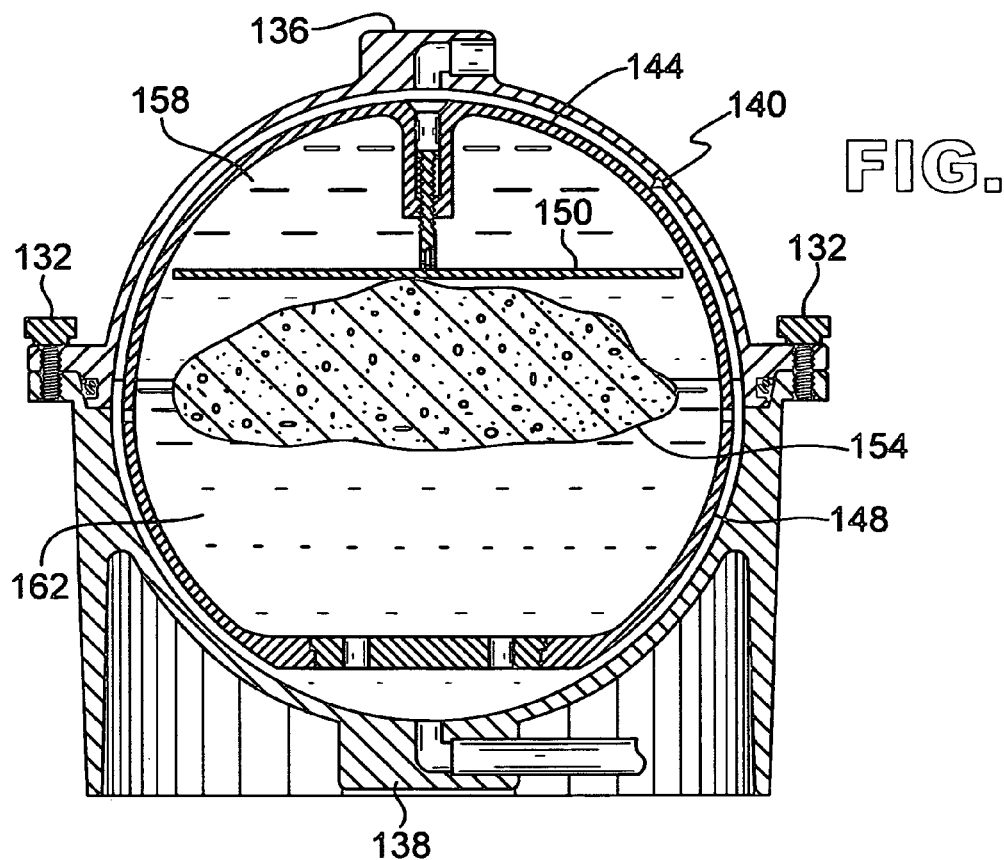
FIG. 14 is a cross-sectional view of the enclosure of FIG. 13 within the housing and the closure covering the housing in a first position.
Figure 15:
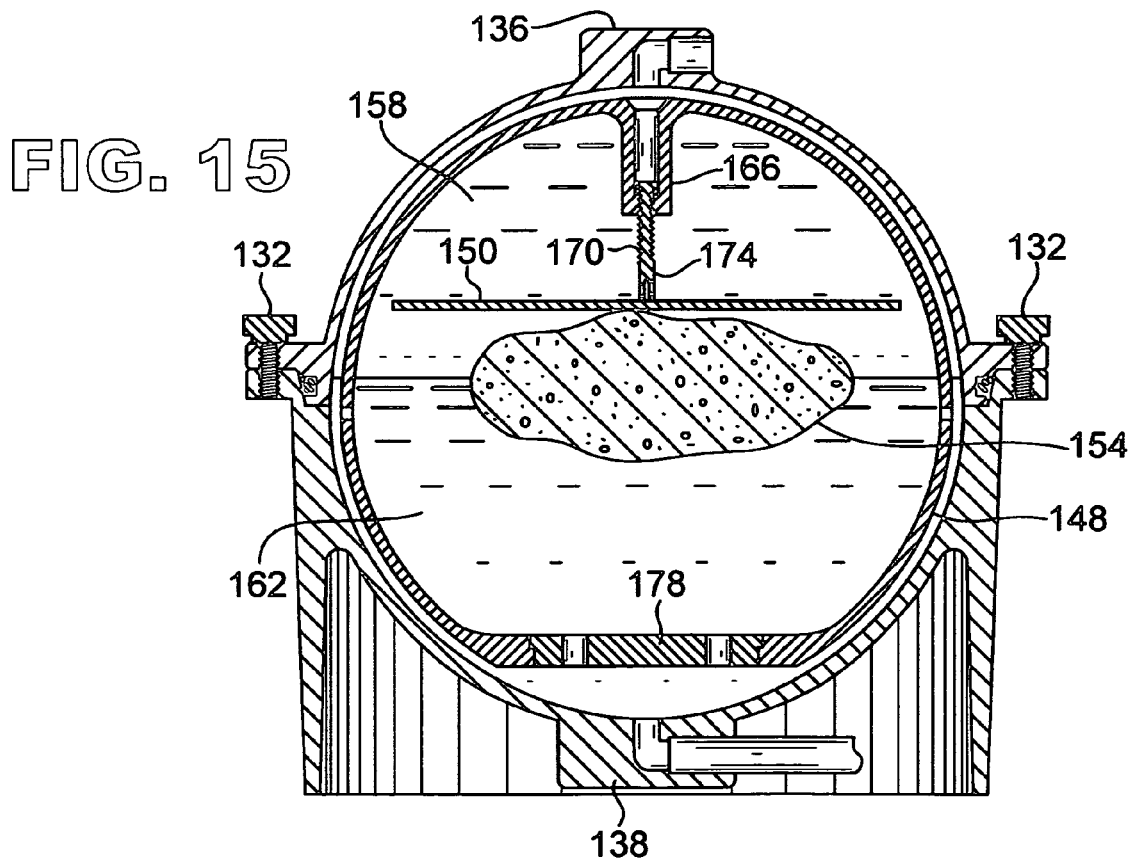
FIG. 15 is a cross-sectional view of the enclosure of FIG. 13 within the housing and the closure covering the housing in a second position.
Figure 16:
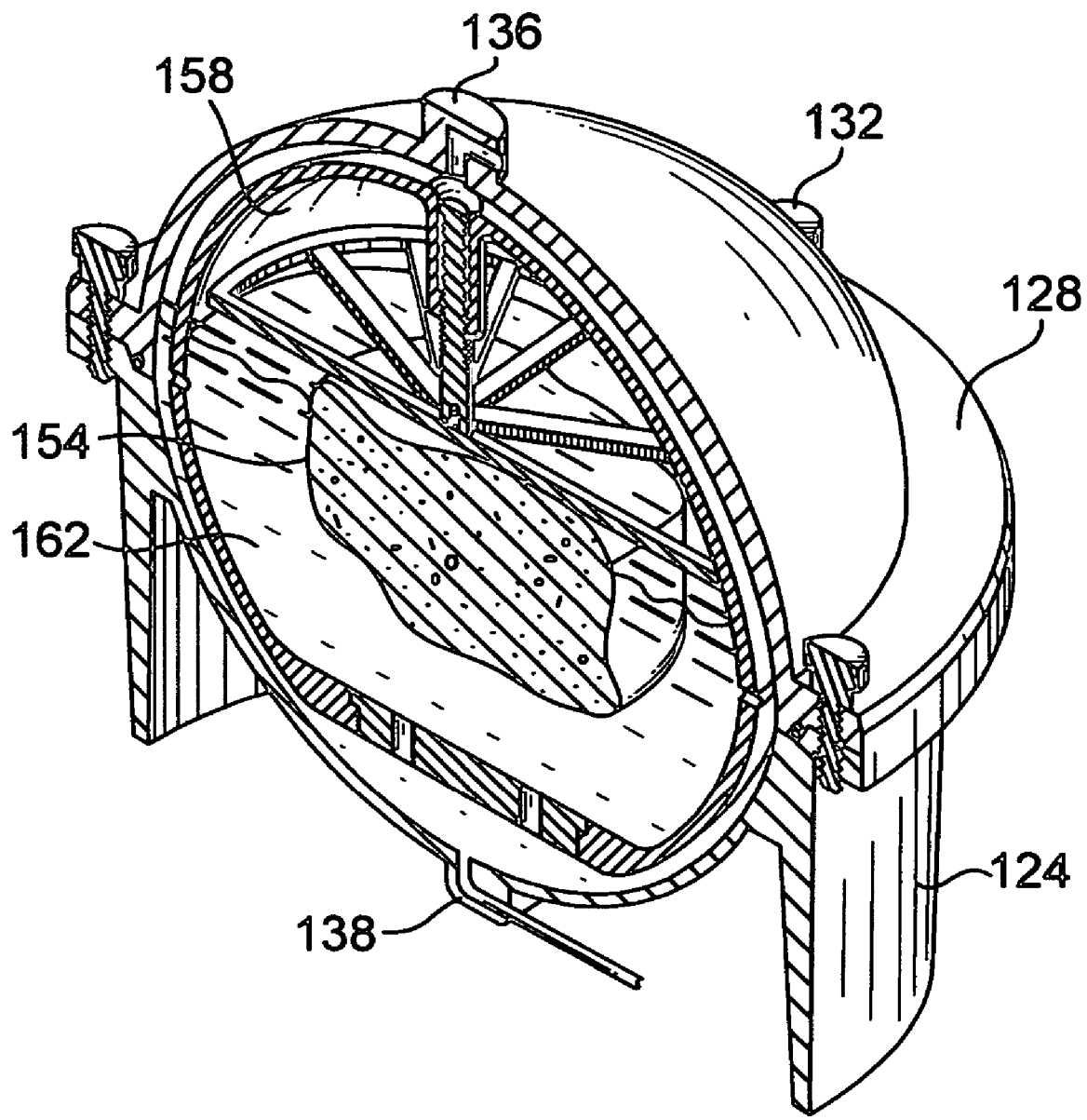
FIG. 16 is a perspective view, partially broken away, of the embodiment of FIG. 14.

An enclosure 140 to be used with the organ preservation container 120 is shown in FIG. 13. The enclosure 140 can have a top portion 144 and a bottom portion 148. The top portion 144 is engageable to the bottom portion 148. Both the top portion 144 and bottom portion 148 are substantially semi-spheroidal, such that the enclosure 140 has a substantially spheroidal shape when the top portion 144 is engaged to the bottom portion 148.

Within the enclosure 140 is a holder 150 which can be in the form of a plate or screen. The holder 150 contacts the organ 154 to maintain the organ 154 at the interface between a first liquid 158 and second liquid 162. A seat 166 can be provided in the top portion 144 of the enclosure 140. The seat 166 has a spring shaft 170 slidably mounted therewithin. A spring 174 cooperates with the spring seat 166 to act on the spring shaft 170. The spring shaft 170 is connected to the holder 150 such that the spring 174 acts on the holder 150 to apply a force to the organ 154. This force will maintain the organ 154 at the appropriate position in the interface of the first liquid 158 and second liquid 162. The spring constant of the spring 174 is selected according to the size and density of the organ 154 and the relative densities of the first liquid 158 and second liquid 162. Additional structure for adjusting the tension of the spring 174 is possible. It is also possible to provide additional calibrated downward force-providing mechanisms, including solenoids, pneumatic systems, and the like. Ballast 178 can be provided in the base of the enclosure 140 in order to provide a mechanism by which the enclosure 140 will right itself if the housing 124 is tilted from the vertical.

Figure 17:
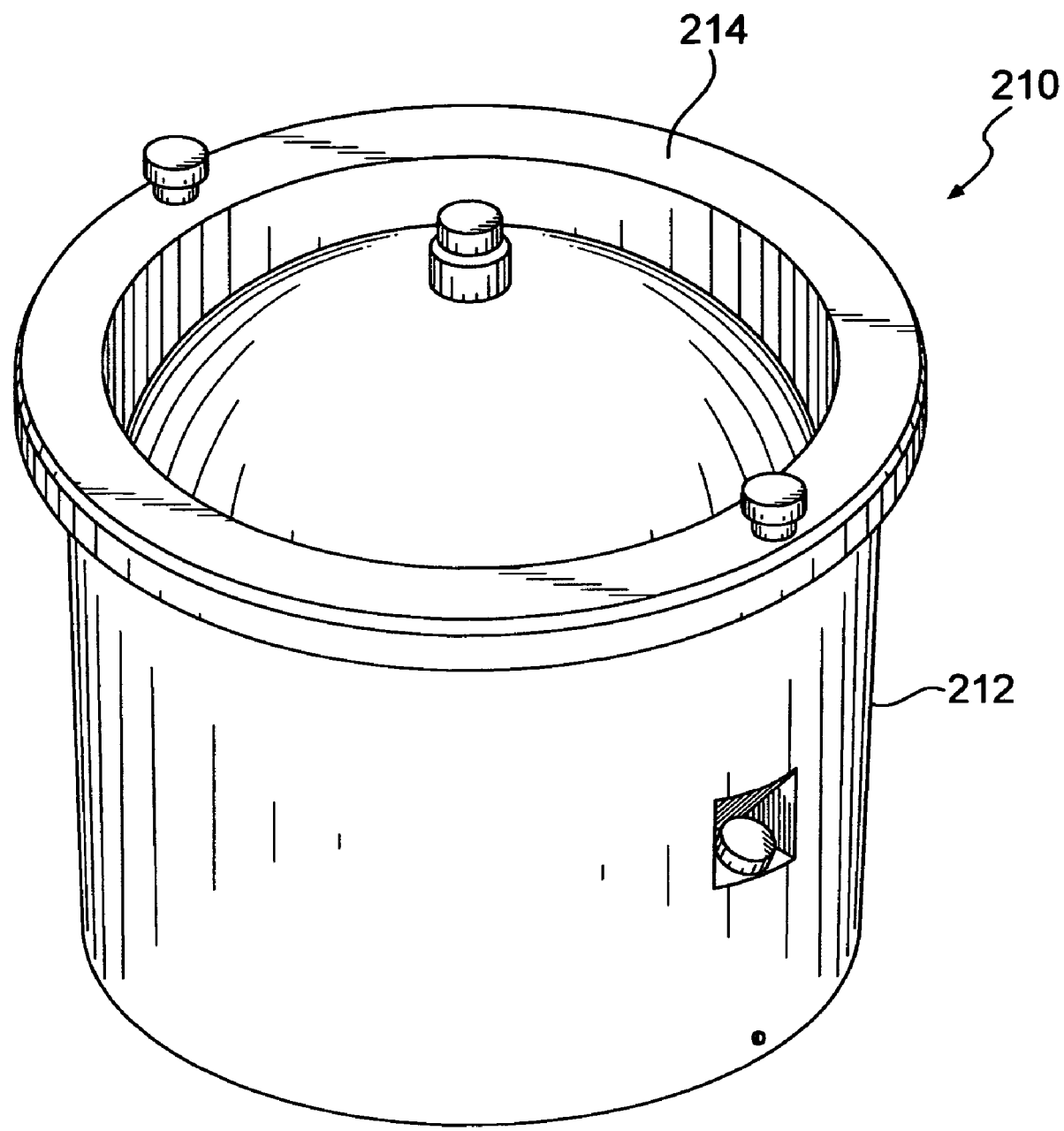
FIG. 17 is a perspective view of an organ preservation container according to the invention.
Figure 18:
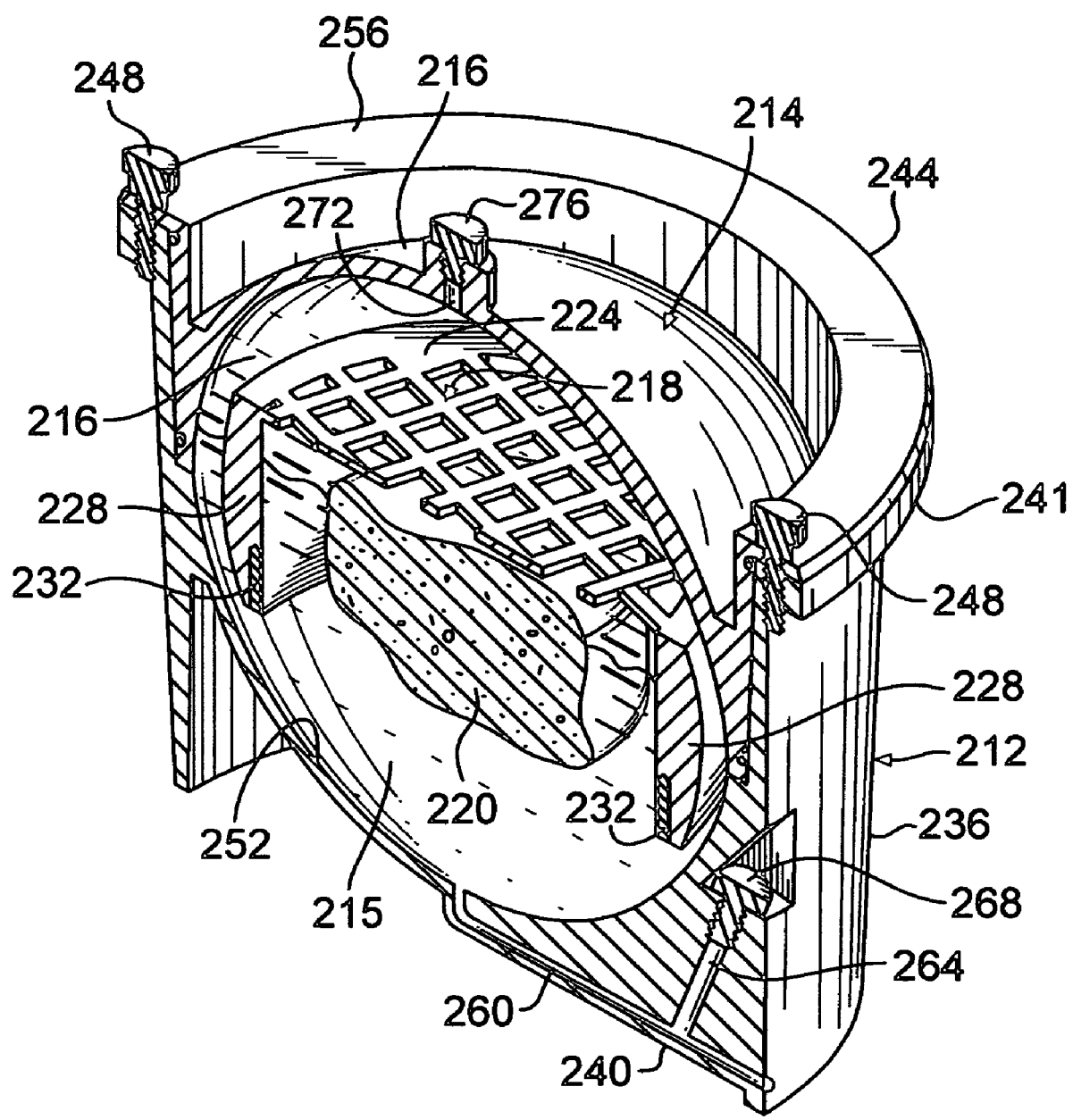
FIG. 18 is a cross-sectional view of the organ preservation container of FIG. 17.

There is shown in FIGS. 17-18, a container 10 for preserving organs. The container has a housing 212 and a closure 214 for hermetically sealing the housing 212. The housing 212 contains liquids such as a preservation solution and an oxygen-dissolving solution. An enclosure 218 within the housing is provided for maintaining an organ 220 partially in the oxygen-dissolving solution and partially in the preservation solution.

The enclosure 218 for maintaining the organ partially in the first liquid and partially in the second liquid can comprise ballast structure and engages the organ and imparts appropriate weight to the organ so that the organ is maintained at the interface between the first liquid and the second liquid.

The enclosure 218 can be a full enclosure or partial enclosure for the organ. In one embodiment, top 224 and depending sides 228 form the enclosure for the organ 220. The top 224 is preferably permeable to permit the free flow of solution into and out of the enclosure 218.

The enclosure has a density that is selected to maintain the organ at the interface between the first liquid and the second liquid. The enclosure 218 has a density selected to maintain the organ 220 partially in the first liquid, such as oxygen-dissolving solution 215, such that the organ receives the oxygen which is necessary for organ maintenance. The density of the enclosure 218 is also selected such that the organ 220 will also be maintained partially in the second liquid, such as preservation solution 216, for optimum organ maintenance. In one aspect, the enclosure 218 has a density such that it maintains the organ with about ⅔ of the organ volume in the oxygen-dissolving solution 215 and about ⅓ of the organ volume in the preservation solution 216. The density of the enclosure 218, however, will be selected depending on the relative densities of the oxygen-dissolving solution 215 and the preservation solution 216. A common oxygen-dissolving solution, perfluorocarbon (PFC), has a density of about 1.95 g/cm$^3$. The density of most organs is approximately 1 g/cm$^3$. In this case, the enclosure has a density of between about 1.5-2.5 g/cm$^3$. The enclosure 218 preferably in this case has a density of about 2 g/cm$^3$.

The appropriate density of the enclosure 218 can be obtained by producing the enclosure 218 from the material with the appropriate density. The enclosure 218 is preferably designed to float upright at all times. It is possible to manufacture the enclosure 218 from one material, such as plastic, and to weight the enclosure 218 with weights 232 such that the average density of the enclosure 218 will be the desired density. The weights 232 can be of any suitable material, such as stainless steel.

The enclosure 218 is shown having a partially-enclosing configuration, that is, with two open sides and bottom such that the organ 220 is only partially contained between the top 224 and depending sides 228 of the enclosure 218. It will be appreciated that other configurations are possible, including an enclosure in which the organ is completely within the enclosure 218. Such an enclosure could have any suitable shape, such as a rectangular or spherical shape, so long as there are sufficient openings in the enclosure to permit the free flow of oxygen-dissolving solution 215 and preservation solution 216 to the organ 220.

In one embodiment, the oxygen-dissolving solution is perfluorocarbon (PFC). Alternatives to PFC are possible. These alternative oxygen-dissolving solutions should be capable of dissolving oxygen and releasing oxygen to the organ over time. The oxygen-dissolving solution must not be harmful to the organ.

The preservation solution can be any suitable preservation solution. One common preservation solution is the University of Wisconsin Preservation Solution, or "UW" Solution. Alternatives to the UW Solution can be used. Such solutions are being developed as replacements or improvements to the UW Solution. These include Hypothermosol® produced by Mediatech, Inc. of Herndon, Va., and Eurocollins Solution.

The housing 212 can be of any suitable design. In the embodiment shown, the housing 212 has sides 236 and base 240. The closure 214 in this embodiment is the top of the housing 212, however, it will be appreciated that the closure 214 could be fashioned smaller and a top provided that is fixed to sides 236. In the embodiment shown, housing 212 has a attachment flange 241 at a top end of sides 236 that is adapted to mate with a cooperating flange 244 on the closure 214. Bolts 248 or other appropriate fastening structure are provided to hermetically secure the closure 214 to the housing 212. The housing 212 and closure 214 together form an open interior for containing the oxygen-dissolving solution 215 and preservation solution 216. The interior wall 252 forming the open interior preferably is substantially spherical. Closure 214 can have a spherical portion 256 to maintain the spherical configuration of the open interior. The spherical configuration provides the same interior geometry no matter what the position of the housing 212, and provides that the organ and enclosure will remain substantially upright when the container 210 is tilted.

The container 210 can include appropriate structure for injecting the liquids and oxygen into the container, or to re-oxygenate the oxygen-dissolving solution 215 in the event that the solution must be re-oxygenated. In one embodiment, an injection port 260 leads from an injection port opening 264 to the interior volume. An injection port closure 268 is used to hermetically seal the port opening 264 against the escape of fluid. The injection port closure 268 can be removed and suitable structure used to inject liquids and/or oxygen into the injection port opening 264 and injection port 260, and thereby into the interior volume of the container. A pressure relief opening 272 can be provided to permit the escape of oxygen gas or liquids from the container. The relief opening 272 can be closed by suitable structure such as relief closure 276.

In operation, the closure 214 is removed and organ 220 is positioned within enclosure 218 and the organ and enclosure 218 are positioned in the interior volume of the housing 212. The closure 214 is then placed onto the housing 212 and bolts 248 are utilized to hermetically secure the closure 214 to the housing 212. Appropriate sealing structure such as o-rings can be provided to facilitate the seal. The interior volume of the housing 212 is then filled with oxygen-dissolving solution 215 and preservation solution 216. The relative amount of each can vary depending on the size of the container 210 and the particular organ being utilized. In one aspect, for pancreas transportation, approximately 350 ml of oxygen-dissolving solution and between about 150-500 ml of preservation solution are used. Some liquid may escape from the relief port 272. If necessary, oxygen can be pumped into the oxygen-dissolving solution 215 through port inlet opening 264. Excess oxygen will escape through the relief port 272. Port closure 268 is then secured to hermetically seal the port opening 264. Relief closure 276 is secured to seal the relief port 272. The organ 220 is then removed at its destination by releasing pressure by removing or loosening the relief closure 276. Bolts 248 are removed and closure 214 is removed from the housing 218. The organ 220 is then removed from the enclosure 218 and placed in alternative storage or is immediately used.

The invention can be provided in other forms and embodiments without departing from the spirit or essential attributes thereof and, accordingly, reference should be had to the following claims, rather than to the foregoing specification, as indicating the scope of the invention.

We claim:

1. An organ preservation container, comprising:
    a gas impermeable housing for containing said organ and at least two liquids having different densities and forming a liquid-liquid interface in said housing;
    a closure for hermetically sealing said housing; and,
    a floating enclosure within said housing, said floating enclosure being unconnected to said housing and rotatable with respect thereto, said floating enclosure having an average density that is greater than the density of one of said liquids and less than the density of the other of said liquids, said floating enclosure engaging said organ and floating in said liquids and maintaining a portion of said organ at said liquid-liquid interface such that said organ will be maintained partially in both of said liquids.

2. The organ preservation container of claim 1, wherein said floating enclosure comprises ballast structure.

3. The organ preservation container of claim 1, wherein said enclosure comprises a portion made of a first material and at least one weight having a density greater than said first material.

4. The organ preservation container of claim 1, wherein said enclosure has an average density of about 2 g/cm$^3$.

5. The organ preservation container of claim 1, wherein said enclosure comprises a top portion and depending side portions, at least said top portion being liquid permeable.

6. The organ preservation container of claim 1, wherein one of said liquids comprises an oxygen-dissolving solution and another of said liquids comprises a preservation solution.

7. The organ preservation container of claim 6, wherein said floating enclosure keeps said organ about ⅔ in said oxygen-dissolving solution and about ⅓ in said preservation solution.

8. The organ preservation container of claim 7, wherein said oxygen-dissolving solution is perfluorocarbon and said preservation solution is UW solution.

9. The organ preservation container of claim 1, wherein said housing and said closure provide a substantially spherical interior volume.

10. The organ preservation container of claim 1, wherein said floating enclosure comprises a substantially spherical enclosure for said organ.

11. The organ preservation container of claim 1, wherein said floating enclosure has a top portion and a bottom portion, said top portion and said bottom portion comprising apertures for permitting the ingress and egress of liquid.

12. The organ preservation container of claim 11, wherein said bottom portion comprises ballast.

13. The organ preservation container of claim 1, wherein said floating enclosure comprises a spherical portion and said housing comprises a spherical interior surface, said floating enclosure being able to rotate within said housing.

14. A method for preserving organs, comprising the steps of:
    providing an organ preservation container comprising a gas impermeable housing for containing said organ and at least two liquids having different densities and forming a liquid-liquid interface in said housing, a closure for hermetically sealing said housing, and floating structure within said housing, said floating structure comprising an enclosure for said organ, said enclosure having an average density greater than the density of one of said liquids and less than the density of the other of said liquids, said floating structure engaging said organ and floating in said liquids while maintaining a portion of said organ at said liquid-liquid interface such that said organ will be maintained partially in both of said liquids, said structure being unconnected to said housing and rotatable with respect thereto;

placing said organ into said floating structure and placing said floating structure in said housing for maintaining said organ at said liquid-liquid interface; and, securing said closure to said housing.

15. The method of claim 14, wherein said floating structure comprises ballast structure.

16. The method of claim 14, wherein said enclosure comprises a portion made of a first material and at least one weight having a density greater than said first material.

17. The method of claim 14, wherein said enclosure has an average density of about 2 grams per cubic centimeter.

18. The method of claim 14, wherein said enclosure has a top portion and depending side portions, at least said top portion being liquid permeable.

19. The method of claim 16, wherein said first material is plastic and said weights comprise metal.

20. The method of claim 14, further comprising the step of injecting a fluid into said container through at least one port.

21. The method of claim 14, wherein one of said liquids comprises an oxygen-dissolving solution and another of said liquids comprises a preservation solution.

22. The method of claim 21, wherein said structure for maintaining keeps said organ about ⅔ in said oxygen-dissolving solution and about 113 in said preservation solution.

23. The method of claim 21, wherein said oxygen-dissolving solution is perfluorocarbon and said preservation solution is UW solution.

24. The method of claim 14, wherein said housing and said closure provide a substantially spherical interior volume.

25. The method of claim 14, wherein said placing step comprises contacting said organ with a force selected to maintain said organ at said liquid-liquid interface.

* * * * *